(12) United States Patent
Hedemann et al.

(10) Patent No.: US 12,714,296 B2
(45) Date of Patent: Aug. 25, 2026

(54) METHOD FOR SUPPLEMENTING A COMPONENT OF A MEDICAL INSTRUMENT

(71) Applicant: KARL STORZ SE & Co KG, Tuttlingen (DE)

(72) Inventors: Lars Hedemann, Tuttlingen (DE); Andreas Heni, Tuttlingen (DE); Markus Kupferschmid, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 1019 days.

(21) Appl. No.: 17/723,122

(22) Filed: Apr. 18, 2022

(65) Prior Publication Data

US 2022/0330798 A1 Oct. 20, 2022

(30) Foreign Application Priority Data

Apr. 19, 2021 (DE) ........................ 102021109864.5

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00096* (2013.01); *A61B 1/0051* (2013.01);
(Continued)

(58) Field of Classification Search
CPC ... A61B 1/018; A61B 1/00096; A61B 1/0051; A61B 1/042; A61B 1/05; A61B 1/0669;
(Continued)

(56) References Cited

U.S. PATENT DOCUMENTS 5,169,568 A * 12/1992 Ainger, III .............. B29C 70/76 600/128
5,540,970 A * 7/1996 Banfield ............ A44B 18/0049 24/444

(Continued)

FOREIGN PATENT DOCUMENTS

CN 102307510 A 1/2012
DE 102009032924 A1 2/2011

(Continued)

OTHER PUBLICATIONS

Machine Translation of Chinese Patent No. CN102307510A to Petersen, "Endoscope having a camera housing and method for making a camera housing," pp. 1-16.

(Continued)

*Primary Examiner* — JaMel M Nelson
*Assistant Examiner* — Erica Hartsell Funk
(74) *Attorney, Agent, or Firm* — Jason H. Vick; Amped IP LLC

(57) ABSTRACT

A method for supplementing a component (20) of a medical instrument (10) by way of a plastic component comprises the steps of inserting (106) the component (20) of the medical instrument (10) into a casting mold (70) and closing (107) the casting mold (70), a first region (72) of a mold surface of the casting mold (70) being placed against the component (20) and a casting chamber (78) remaining between a second region (74) of the mold surface of the casting mold (70) and the component (20); a step of supplying (108) a liquid plastic to the casting chamber (76); and a step of coupling (111) electromagnetic radiation into the liquid plastic within the casting chamber (76) in order to trigger a solidification of the plastic and in order to form the plastic component.

9 Claims, 7 Drawing Sheets

(51) Int. Cl.

| | |
|---|---|
| ***A61B 1/005*** | (2006.01) |
| ***A61B 1/04*** | (2006.01) |
| ***A61B 1/05*** | (2006.01) |
| ***A61B 1/06*** | (2006.01) |
| ***A61B 1/07*** | (2006.01) |
| ***G02B 23/24*** | (2006.01) |

(52) U.S. Cl.
CPC ................ *A61B 1/042* (2013.01); *A61B 1/05* (2013.01); *A61B 1/0669* (2013.01); *A61B 1/0676* (2013.01); *A61B 1/0684* (2013.01); *A61B 1/07* (2013.01); *G02B 23/2469* (2013.01)

(58) Field of Classification Search
CPC ....... A61B 1/0676; A61B 1/0684; A61B 1/07; A61B 1/0125; A61B 1/015; A61B 1/005; G02B 23/2469; B29C 45/14; B29C 45/14008; B29C 45/14065; B29C 45/14286
See application file for complete search history.

(56) References Cited

U.S. PATENT DOCUMENTS

| | | | |
|---|---|---|---|
| 9,125,582 B2 | 9/2015 | Petersen | |
| 9,925,696 B2 | 3/2018 | Rist et al. | |
| 2014/0066709 A1* | 3/2014 | Mirza ............. | A61B 17/32002 600/106 |

FOREIGN PATENT DOCUMENTS

| | | |
|---|---|---|
| DE | 102012105564 A1 | 1/2014 |
| DE | 102016014519 A1 | 6/2018 |
| WO | 2013024146 A1 | 2/2013 |

OTHER PUBLICATIONS

Butzek, German Search Report, Oct. 15, 2021, pp. 1-5, DPMA, Munich.

* cited by examiner 70
82
82
86
96
72
76
76
72
84
24
20
30
40
32
96
86
74
80
94
92
90
74
54
88
N
S 70
82
72
76
76
72
84
86
96
24
20
50
30
40
32
94
92
90
74
96
86
74
80
88
N
S

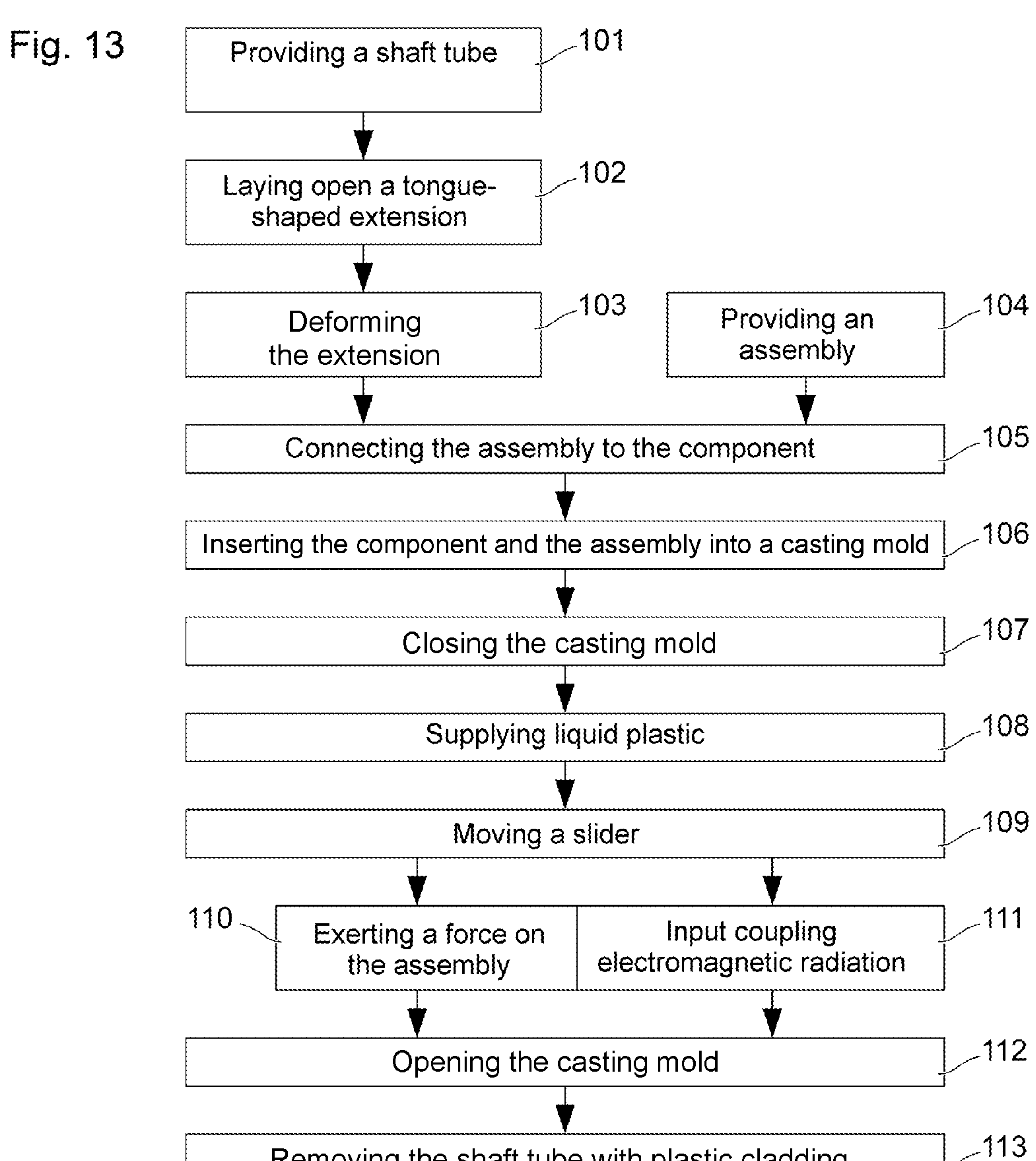
Fig. 13
Providing a shaft tube
101
Laying open a tongue-shaped extension
102
Deforming the extension
103
Providing an assembly
104
Connecting the assembly to the component
105
Inserting the component and the assembly into a casting mold
106
Closing the casting mold
107
Supplying liquid plastic
108
Moving a slider
109
110
Exerting a force on the assembly
Input coupling electromagnetic radiation
111
Opening the casting mold
112
Removing the shaft tube with plastic cladding
113

METHOD FOR SUPPLEMENTING A COMPONENT OF A MEDICAL INSTRUMENT

CROSS REFERENCE TO RELATED APPLICATIONS

This application claims priority to German Patent Application No. 102021109864.5, filed Apr. 19, 2021, and entitled, "Verfahren zum Ergänzen eines Bauteils eines medizinischen Instruments," and is incorporated herein by reference.

TECHNICAL FIELD OF THE INVENTION

The present invention relates to a method for producing a medical instrument, specifically for supplementing a component of a medical instrument with a plastic component. Further, the present invention relates to a casting mold for supplementing a component of a medical instrument with a plastic component. Further, the present invention relates to a medical instrument which may be produced by means of the method and/or with the aid of the casting mold in particular.

BACKGROUND OF THE INVENTION

Some medical instruments have a complex structure and a complex geometry. The distal end of the rigid or partly or completely flexible endoscope is but one example. A light source for producing illumination light or an end of an optical waveguide for transmitting illumination light to the distal end, an objective lens and ever more frequently an image sensor and the distal ends of one or more work and/or rinsing channels, too, are arranged in a very tight space and are mechanically permanently and robustly connected. As a rule, the surface of the endoscope—apart from inlets and outlets of fluid and work channels—should furthermore also be fluid tight or hermetically sealed at the distal end.

One approach consists in the use of a cap structural element with openings, into which the light source, the camera, etc. are inserted. Another technical approach consists in "overmolding" the components or assemblies at the distal end of the endoscope, that is to say, enveloping these within the scope of an injection molding method. However, temperature gradients and temperatures that might damage electronic structural elements arise in this process.

SUMMARY OF THE INVENTION

An object of the present invention consists in the facilitation of an improved production of a medical instrument.

Embodiments of the present invention are based on the concept of replacing the use of thermoplastic plastic with the use of a plastic that at the outset is liquid at room temperature and the solidification or curing of which is brought about or triggered by electromagnetic radiation, for example blue or ultraviolet light. Further, embodiments of the present invention are based on the concept of mechanically connecting an assembly, for example consisting of light source and camera, to the distal end of the shaft tube already before overmolding with plastic.

A method for supplementing a component of a medical instrument by way of a plastic component comprises the steps of inserting the component of the medical instrument into a casting mold and closing the casting mold, a first region of a mold surface of the casting mold being placed against the component and a casting chamber remaining between a second region of the mold surface of the casting mold and the component; a step of supplying a liquid plastic to the casting chamber; and a step of coupling electromagnetic radiation into the liquid plastic within the casting chamber in order to bring about or trigger a solidification of the plastic and in order to form the plastic component.

In particular, the method is suitable for supplementing a shaft or a shaft tube of an endoscope or any other metallic component. Further, the method can be suitable for supplementing a component made of a plastic or any other material.

The casting mold may have a plurality of mold parts, a cavity remaining between these in the closed state. This chamber is bounded by an inner surface of the casting mold, which is referred to as a mold surface below. After the component of the medical instrument has been inserted into the casting mold, said component takes up part of the cavity. In this case, the first region of the mold surface contacts the component in planar or line-shaped fashion.

In addition to the second region of the mold surface, the casting chamber is also formed by a surface region of the component not contacting the mold surface of the casting mold. When the liquid plastic is supplied to the casting chamber, said casting chamber is filled, in particular completely. The casting chamber can merge into a lumen or a cavity within the component. This lumen or this cavity may be filled completely or in part within the scope of the method.

Input coupling electromagnetic radiation comprises input coupling of in particular ultraviolet light or visible light in the spectral range perceived as blue by a healthy human eye. The electromagnetic radiation may bring about solidification, for example polymerization, directly or may only trigger this by virtue of for example producing or generating a catalyst that brings about a polymerization or any other chemical reaction.

The thermal load can be significantly reduced or avoided by the use of a plastic which is liquid at room temperature and unlike a thermoplastic does not transition into the solid state by cooling but transitions by a chemical process triggered or driven by electromagnetic radiation, in particular. For this reason, electronic structural elements which would be damaged by the temperatures and temperature gradients arising in conventional casting methods with thermoplastics can also be inserted into the casting mold with the component, for example.

In a method as described here, the electromagnetic radiation is coupled into the liquid plastic in particular through a mold insert, transparent to electromagnetic radiation, in a mold part or through a transparent mold part or through a transparent slider or through a transparent insert in a slider for closing a supply opening.

A transparent mold insert in a mold part forms part of the mold surface of the casting mold, that is to say directly adjoins the casting chamber. A light source that is integrated into the casting mold or a light source that is arranged outside of the casting mold and optically coupled with the transparent mold insert can produce light that triggers or brings about the solidification of the liquid plastic, said light penetrating into the liquid plastic through the transparent mold insert.

A corresponding statement applies to a transparent mold part which not only has a transparent mold insert but which is completely transparent to the electromagnetic radiation.

A transparent slider or a slider with a transparent insert is movably arranged, for example, in a drilled hole or in any other cylindrical channel that merges into the casting chamber. The opening of the drilled hole or of the cylindrical channel to the casting chamber forms the supply opening for supplying the liquid plastic into the casting chamber The end of the slider facing the casting chamber completely closes off the supply opening—apart from geometric play required for mechanical ease of movement. A casting chamber-facing portion of the outer surface of the slider which adjoins the casting chamber forms a part of the mold surface of the casting mold.

The transparent slider or the transparent insert of the slider can be optically coupled with a light source or any other source for producing the electromagnetic radiation, for example by way of an optical waveguide or by way of other optical elements. The light source or the other source of electromagnetic radiation can be mechanically rigidly coupled to, or integrated in, the slider.

Should the slider be formed (largely) from a transparent material, the lateral surface of the slider is coated in particular in order to prevent an emergence of the electromagnetic radiation there into a thin gap surrounding the slider and hence prevent a solidification of liquid plastic present there.

A transparent mold insert or transparent mold part can facilitate extensive and uniform coupling of the electromagnetic radiation into the casting chamber. The use of a transparent slider or a slider with a transparent insert can permit an otherwise conventional or largely conventional embodiment of a casting mold.

In the case of a method as described here, the liquid plastic is supplied through a component from an end of this component facing away from the casting chamber, in particular, to said casting chamber.

Particularly if the component is in the form of a tube or has a drilled through-hole or any other channel that reaches up to the casting chamber and, on the other hand, reaches out of the casting mold or at least reaches as far as the outer surface of the casting mold, liquid plastic can be supplied to the casting chamber through the lumen of the tube or drilled through-hole or channel. In this case, the casting mold need not have a supply channel for supplying liquid plastic.

In the case of a method as described here, the electromagnetic radiation is coupled into the casting chamber through a component, in particular from an end of this component here facing away from the casting chamber.

Particularly if the component is in the form of a tube or has a drilled through-hole or any other channel that reaches up to the casting chamber and, on the other hand, reaches out of the casting mold or at least reaches as far as the outer surface of the casting mold, coupling of the electromagnetic radiation into the liquid plastic in the casting chamber through the component may be possible through the lumen of the tube or drilled through-hole or channel. A transparent mold insert in the mold part or a transparent mold part or a transparent slider or a transparent insert in a slider may be superfluous in this case.

In the case of the method as described here, the insertion of the component comprises, in particular, an insertion of an assembly mechanically connected to the component into the casting mold.

The component is a shaft tube in particular, for example a shaft tube of an endoscope or exoscope.

A method for supplementing a shaft tube and an assembly of a medical instrument with a plastic component comprises a step of providing a shaft tube with a distal end, mechanically connecting an assembly to the distal end of the shaft tube by way of a connecting device; steps of inserting the shaft tube with the assembly into a casting mold and of closing the casting mold, a predetermined region of the outer surface of the assembly contacting a mold surface of the casting mold; a step of supplying a liquid plastic into the casting mold, the liquid plastic wetting the distal end of the shaft tube and the outer surface of the assembly; and a step of solidifying the liquid plastic, the solidified plastic forming the plastic component and creating a further mechanical connection of the assembly to the distal end of the shaft tube.

In particular, the medical instrument is an endoscope or exoscope. In particular, the shaft tube forms the mechanically supporting structure of the shaft of the endoscope.

In particular, the shaft tube is made of metal. Alternatively, the shaft tube can be made of a plastic or any other material. The shaft tube can be straight or curved, and can be completely rigid or can be partly or completely flexible. The assembly may comprise one or more structural elements. The predetermined region of the outer surface of the assembly in particular comprises a light-exit surface of a light source or a light-exit surface at a distal end of an optical waveguide and/or a light-entrance surface of an object and/or a camera for creating and capturing an image.

In particular, the casting mold comprises a plurality of mold parts which enclose a cavity and the inner surfaces of which form the mold surface bounding the cavity. After the shaft tube has been inserted into the casting mold and the casting mold has been closed, the shaft tube in particular protrudes from the casting mold or reaches an outer surface of said casting mold. Alternatively, the shaft tube can be arranged completely within the cavity of the casting mold. After the casting mold has been closed, a lateral surface region of the shaft tube, in particular, contacts a first region of the mold surface of the casting mold. A second region of the mold surface of the casting mold bounds a casting chamber together with a region of the surface of the shaft tube not contacting the molding surface of the casting mold, the liquid plastic being supplied to this casting chamber and said liquid plastic solidifying in this casting chamber.

If the liquid plastic is a thermoplastic, it is solidified by cooling. Alternatively, the liquid plastic can be solidified in any other way, for example by polymerization. In this case, solidification can be triggered or caused by radiating in ultraviolet light or light in the spectral range perceived as blue by a healthy human eye or any other electromagnetic radiation.

The mechanical connection of the assembly to the distal end of the shaft tube by way of the connecting device renders a separate mechanical fixation, for example by way of the slider or by way of a feature of the mold, superfluous. As a result, it is possible to avoid disadvantages such as cavities or recesses remaining after casting, which may reach up to the assembly.

It is possible to provide a single connecting device or a plurality of connecting devices for mechanically connecting the distal end of the shaft tube to one or more assemblies. By way of example, provision can be made of a first connecting device for mechanically connecting an assembly comprising at least one image sensor to the distal end of the shaft tube and a second connecting device for mechanically connecting an assembly comprising at least one light-emitting diode or any other light source to the distal end of the shaft tube.

In the case of a method as described here, at least either the insertion of the shaft tube with the assembly or the closing of the casting mold in particular comprises an elastic deformation of the connecting device such that an elastic restoring force of the connecting device presses the predetermined region of the outer surface of the assembly against the mold surface of the casting mold.

The elastic deformation may be small. In particular, the elastic deformation is only dimensioned such that, even within the manufacturing tolerances of the shaft tube, the connecting device and the assembly, the predetermined region of the outer surface of the assembly reliably contacts the mold surface of the casting mold.

As a result of the predetermined region of the outer surface of the assembly contacting the mold surface of the casting mold, it is possible to avoid an ingress of the liquid plastic into a gap between the predetermined region of the outer surface of the assembly and the mold surface of the casting mold, or restrict said ingress to a sufficiently thin film.

In a method as described here, the provision of the shaft tube comprises a formation of the connecting device as a tongue-shaped extension of the shaft tube, the mechanical connecting of the assembly to the distal end of the shaft tube comprising a mechanical connecting to a distal end of the tongue-shaped extension.

By way of example, mechanically connecting the assembly to the distal end of the shaft tube is implemented for example by adhesive bonding, soldering or welding, or in interlocking fashion, for instance by a crimping procedure.

Designing the connecting device as a tongue-shaped extension of the shaft tube creates a particularly simple and at the same time mechanically robust and permanent connecting device. By way of example, a C-shaped region is removed from an end region of a tube by milling or any other machining method or by laser cutting or by punching or by way of any other method, and so only the tongue-shaped extension remains in an end section of the original tube.

In a method as described here, the formation of the connecting device comprises in particular a plastic deformation of the tongue-shaped extension.

The tongue-shaped extension is in particular deformed away from the lateral surface of the original tube and into its lumen. Within the contour of the shaft tube continued distally, this can facilitate complete cladding of the connecting device by the plastic.

Further, the tongue-shaped extension can be plastically deformed in order to set a predetermined spatial orientation of the assembly to be connected to the distal end of the tongue-shaped extension. Further, the tongue-shaped extension can be deformed in order to facilitate or create an interlocking connection of the assembly to the distal end of the tongue-shaped extension, for example in the form of a crimp connection.

A method as described here further comprises, in particular, mechanically or magnetically exerting a force on the assembly while the liquid plastic solidifies.

The force can be generated by an elastic restoring force of the connecting device elastically deformed when the shaft tube with the assembly is inserted into the casting mold or when said casting mold is closed. If the assembly itself or the connecting device is magnetic (in particular ferromagnetic) or magnetizable (in particular paramagnetic) or mechanically connected to a magnetic or magnetizable body, a force may alternatively or additionally be exerted by one or more magnets which may be arranged in or on the casting mold.

Alternatively or in addition, a force may be exerted mechanically on the assembly, for example by way of a feature of the casting mold or by way of an accelerated movement, especially as centrifugal force.

The force may hold the assembly in a predetermined position during the solidification of the liquid plastic, and hence permanently, a light-entrance surface or light-exit surface of the assembly for example contacting a mold surface of the casting mold in said predetermined position.

In the case of the method as described here, connecting the assembly to the connecting device restricts in particular one, two, three, four, five or six degrees of freedom of the movement of the assembly relative to the distal end of the shaft tube.

If the connecting device restricts fewer than six degrees of freedom of the movement of the assembly relative to the distal end of the shaft tube, one or more further degrees of freedom may be restricted in another way, for example by exerting a force on the assembly.

In the case of a method as described here, the insertion of the component into the casting mold comprises, in particular, an insertion of an assembly mechanically connected to the component, said assembly having at least an image sensor or any other sensor for acquiring one or more measured values or a light-emitting diode for generating illumination light or any other light source or a distal end region of a work channel or rinsing channel or of an optical waveguide, or a handling device.

The image sensor may be part of a camera or any other unit made of objective lens and image sensor. The light-emitting diode may be part of a light source with one or more light-emitting diodes and one or more lenses or other devices for shaping an illumination light beam. A camera or a light-emitting diode or a light source is completely enclosed, in particular laterally, by the plastic component, the plastic component being integrally bonded to a part of the surface of the camera or of the light-emitting diode or of the light source. The assembly may comprise a plurality of image sensors and/or a plurality of light-emitting diodes. Alternatively or in addition, the assembly may comprise one or more other sensors for acquiring measured values, for example a pressure sensor for registering the pressure within a cavity while a fluid is rinsed-in, or at any other time.

A distal end face of the camera which comprises a light-entrance surface is not covered by the plastic component in particular. A distal end surface of a light-emitting diode or light source, which comprises a light-exit surface in particular, is in particular not covered by the plastic component. Alternatively, the light-exit surface of the light-emitting diode or light source is covered by the plastic component, specifically by a layer formed by the plastic component with a predetermined thickness of a few tenths of a millimeter, for example. This layer may protect the light-emitting diode or light source from moisture or other environmental influences. A distal end surface of an end region of the work channel or rinsing channel or of an optical waveguide, which in particular comprises an opening to the work channel or rinsing channel or a light-exit surface of the optical waveguide, is in particular not covered by the plastic component.

In a method as described here, the insertion of the component into the casting mold comprises, in particular, an insertion of an electronic assembly for arrangement on a proximal end of the endo scope or the insertion of a joint region.

The plastic component may protect the electronic assembly or the joint region from a fluid and/or provide it with a predetermined external surface.

In a method as described here, the supply of the liquid plastic comprises, in particular, filling a laterally arranged opening in the shaft tube.

The laterally arranged opening in the shaft tube may facilitate coupling of electromagnetic radiation into the shaft tube. By filling the laterally arranged opening in the shaft tube, the laterally arranged opening can be closed and interlocking connection of the solidified plastic with the shaft tube can be created at the same time after the liquid plastic has solidified.

A casting mold for supplementing a component of a medical instrument with a plastic component comprises a cavity, with a first region of a mold surface of the cavity being provided for contacting a surface region of the component, a second region of the mold surface of the cavity and the component enclosing a casting chamber to be filled with plastic and at least either a mold part of the casting mold or a slider for closing a supply channel for supplying plastic into the casting chamber being formed to be at least partly transparent to electromagnetic radiation for the purposes of triggering or causing the formation of the plastic component by solidification of a liquid plastic filled into the casting chamber.

In particular, the casting mold is provided and formed for one of the methods described herein. However, the methods described herein can also be carried out with casting molds that have different features, properties and functions. The methods described here can be carried out using the casting mold or using other casting molds with deviating features, properties and methods.

In particular, the casting mold is designed to supplement a metallic component of a medical instrument, for example an endoscope, exoscope or surgical microscope. The component can be tubular, for example be a straight or curved, rigid, or partly or completely flexible shaft tube. In this case, the casting mold can be provided for supplementing or adding plastic to a proximal or distal end of the shaft tube.

The cavity is largely or completely enclosed by one or more mold parts of the casting mold. The cavity is partly taken up by the component during casting in the case of the intended use. The first region of the mold surface of the cavity, which is provided for contacting a corresponding surface region of the component, can be planar or line shaped. In particular, the casting chamber is a part of the cavity not taken up by the component.

The at least partly transparent design of one or more mold parts of the casting mold or of one or more sliders for closing supply channels facilitates input coupling of electromagnetic radiation, in particular ultraviolet light or light within a spectral range that is perceived as a blue by a healthy human eye. Triggering or bringing about the solidification of a liquid plastic can facilitate supplementing a component at room temperature. Damaging influences of temperatures and temperature gradients can be avoided as a result.

A mold part of a casting mold as described here comprises, in particular, a mold insert made of a material transparent to the electromagnetic radiation.

The mold insert can form part of the mold part and can be securely connected or movable relative thereto. The form insert forms at least part of the second region of the mold surface of the cavity and consequently directly adjoins the plastic, to be solidified, which is supplied to the casting mold in liquid form.

A mold part of a casting mold as described here is, in particular, made of a material transparent to the electromagnetic radiation.

Making an entire tool from a material transparent to the electromagnetic radiation can facilitate particularly large-area coupling of the electromagnetic radiation into the liquid plastic to be solidified.

In a casting mold as described here, the slider, in particular, comprises a constituent part made of a material transparent to the electromagnetic radiation.

By way of example, the slider comprises a rod-shaped or cylindrical constituent part made of a transparent material, which is surrounded by a metal sleeve. In particular, both the transparent constituent part and the sleeve each form part of the surface of the casting chamber. Hence, the transparent constituent part directly adjoins the casting chamber, and electromagnetic radiation can be coupled through the transparent constituent part into the liquid plastic to be solidified within the casting chamber.

In a casting mold as described here, the slider, in particular, is made of a material transparent to the electromagnetic radiation.

Both if the entire slider is made of transparent material and if the slider has a constituent part made of a transparent material, the end of the slider or transparent constituent part of the slider facing away from the casting chamber can be coupled to one or more light sources by way of an optical waveguide, a light-guiding cable, a lens, a mirror and/or other optical structural elements.

Incidentally, making the entire slider or constituent part of the slider from a material transparent to the electromagnetic radiation can facilitate a conventional embodiment of the casting mold, in particular an embodiment of the remaining casting mold made of material not transparent to the electromagnetic radiation.

In the case of a casting mold as described here, the surface of the casting chamber is made, in particular, from polytetrafluoroethylene or fluorinated ethylene propylene or an amorphous fluoropolymer or any other material which does not integrally bond with the plastic.

Polytetrafluoroethylene is also known as polytetrafluoroethene, the abbreviation PTFE and, inter alia, by the trade name Teflon. Amorphous fluoropolymers are also distributed under the trade name Teflon AF.

Only the second region of the mold surface of the casting mold or else the first region of the mold surface of the casting mold can be made of one of the aforementioned materials. In this case, it may be only a thin coating with one of the aforementioned materials that is provided. Alternatively, one or more mold parts of the casting mold or one or more mold inserts in mold parts of the casting mold may be made partly or in full of one of the aforementioned materials.

A medical instrument comprises a shaft tube with a distal end, an assembly at the distal end of the shaft tube, a connecting device which mechanically connects the assembly to the shaft tube, and a plastic cladding which at least partly surrounds the assembly, which is integrally bonded to the outer surface of the assembly, which surrounds the connecting device, and which likewise mechanically rigidly connects the assembly to the shaft tube.

In particular, the medical instrument is an endoscope or exoscope or a surgical microscope. The shaft tube can be straight or curved and can be rigid or can be partly or completely flexible. The shaft tube may be the main structure element of the shaft of the medical instrument.

In particular, the medical instrument may be produced by means of a method as described herein and/or by means of a casting mold as described herein. A method as described herein and a casting mold as described herein are provided and designed, in particular, for the production of a medical instrument as described herein.

The plastic cladding is a plastic component which surrounds the assembly, in particular laterally. A predetermined surface region, in particular a light-exit surface or a light-entrance surface of the assembly, may remain uncovered by the plastic cladding, i.e., might not be covered, but may itself form part of the outer surface of the medical instrument. The connecting device can be surrounded by the plastic cladding, in particular laterally in full, that is to say in a sleeve-like or hose-like or lateral manner. To this end, the connecting device in particular is not arranged or only partly arranged on the outer surface of the medical instrument.

The connecting device can create a mechanical connection between the assembly and the shaft tube even before the production of the plastic cladding. This facilitates common handling of the assembly with this shaft tube and a predetermined arrangement of the assembly in a casting mold for producing the plastic cladding purely by way of a predetermined arrangement of the shaft tube. Therefore, the medical instrument has no cutouts for example, used in a conventional method by pins, sliders or other mechanical devices to hold the assembly in the desired predetermined position during the production of the plastic cladding.

In a medical instrument as described here, the connecting device is formed from a tongue-shaped extension of the shaft tube in particular.

The tongue-shaped extension is formed in particular by removing a C-shaped end region of a tube such that only the tongue-shaped extension remains.

The connecting device may further be formed by plastic deformation, in particular bending of the tongue-shaped extension. Bending the tongue-shaped extension can distance the latter from the external contours of the shaft tube continued distally and can facilitate a complete plastic cladding of the connecting device within the distally continued contour of the shaft tube.

The plastic deformation of the tongue-shaped extension can further facilitate desired positioning and alignment of the assembly relative to the distal end of the shaft tube. The plastic deformation of the tongue-shaped extension can further facilitate or create the mechanical connection of the assembly to the tongue-shaped extension (for example by way of a crimping procedure).

A plurality of tongue-shaped extensions, which each form a connecting device, may be provided. Each tongue-shaped extension can mechanically connect a distinct assembly to the distal end of the shaft tube. Alternatively, a plurality of tongue-shaped extensions can mechanically connect the same assembly to the distal end of the shaft tube.

A medical instrument as described here further comprises, in particular, a laterally arranged opening in the shaft tube, the plastic of the plastic cladding at least partly filling the shaft tube and completely filling the laterally arranged opening.

By way of example, the laterally arranged opening is formed as a transverse drilled hole orthogonal to a longitudinal axis of the shaft tube. It is possible to provide only one or more openings, in particular two openings arranged opposite one another.

During the production of the plastic cladding, the opening can facilitate the supply of liquid plastic and/or input coupling of electromagnetic radiation for triggering or bringing about a solidification of initially liquid plastic. Further, the solidified plastic filling the opening can create an interlocking connection between the plastic cladding and the shaft tube.

In the case of medical instrument as described here, the assembly in particular at least comprises either an image sensor or a light-emitting diode or any other light source for producing illumination light or an end region of an optical waveguide or a distal end region of a work channel or rinsing channel.

The end region is, in particular, the distal end region of the optical waveguide or of the work channel or rinsing channel.

A medical instrument as described here may comprise a heat pipe for dissipating waste heat of an assembly, in particular for transferring waste heat of an assembly at a distal end of an endo scope to a proximal end of the endo scope.

The distal end of the heat pipe is mechanically connected to the assembly, in particular, contacts the latter or is arranged in the direct vicinity of the assembly at a small distance therefrom in relation to the remaining dimensions of the assembly and the heat pipe.

A medical instrument as described here in particular further comprises a heat pipe, the connecting device being formed by the heat pipe or being mechanically and thermally directly connected to the heat pipe.

A medical instrument, as described here, is in particular an endoscope or laryngoscope with a rigid, partly flexible, or completely flexible shaft.

BRIEF DESCRIPTION OF THE DRAWINGS

Embodiments are described in more detail below with reference to the accompanying figures, in which:

FIG. 13 shows a schematic flow chart.

DESCRIPTION OF THE REPRESENTATIVE EMBODIMENTS

Figure 1:
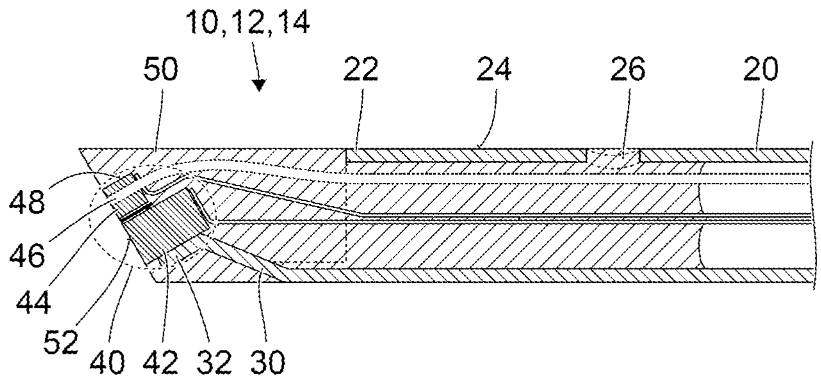
FIG. 1 shows a schematic illustration of a distal end of an endoscope.

FIG. 1 shows a schematic illustration of a section through a distal end region 12 of an endoscope 10, specifically of the shaft 14 of the endoscope 10. The shaft 14, or at least its distal end region 12 shown in FIG. 1, is rigid and straight. Alternatively, the shaft 14 may be flexible, either flexible in sections or completely flexible, with the distal end region in particular also having a rigid embodiment in this case.

The shaft 14 comprises a shaft tube 20 with an, in particular, annular cross section. The shaft tube 20 has a distal end 22 in the form of an annular edge. In the depicted example, the annular edge forming the end 22 is located in a plane orthogonal to a longitudinal axis of the shaft tube 20 and orthogonal to the plane of the drawing of FIG. 1.

The lateral surface 24 of the shaft tube 20 has the shape of a lateral cylinder surface. As indicated in FIG. 1, the lateral surface 24 of the shaft tube 20 can be laid open or, deviating from the depiction in FIG. 1, can be surrounded by one or more further layers with electrical, chemical and/or mechanical functions.

In the depicted example, the shaft tube 20 has a lateral opening 26. The lateral opening 26 is a drilled hole in particular, the axis of which is orthogonal to the longitudinal axis of the shaft tube 20 and intersects the latter.

A tongue-shaped extension 30 extends the distal end 22 of the shaft tube 20 distally at one location. An assembly 40 is fastened to a distal end 32 of the tongue-shaped extension 30. In the depicted example, the assembly 40 comprises a camera unit 42 and a light source 44. The camera unit 42 comprises an objective lens for producing a real image and an image sensor for capturing the real image and for generating an image signal that represents the captured image. In particular, the light source 44 comprises one or more light-emitting diodes for producing illumination light.

Optionally, the assembly 40 may comprise further components, for example a distal end region 46 of a work channel or rinsing channel indicated in FIG. 1 by dashed lines.

A lateral surface region 48 of the assembly 40 is covered by a plastic cladding 50 and is integrally bonded to the latter in particular. The plastic cladding 50 extends up to the distal end 22 of the shaft tube 20 in the proximal direction. Further, the plastic cladding 50 projects into the shaft tube and fills the latter up to the point proximal of the lateral opening 26. In the process, the plastic cladding also fills the lateral opening 26 in the shaft tube 20. This creates an interlocking connection to complement the integral bonding between the plastic cladding 50 on the one hand and the distal end face of the shaft tube at its distal end 22 and the inner surface of the shaft tube 20 on the other hand.

The plastic cladding 50 does not cover a distal end surface 52 of the assembly 40 which, in particular, comprises a light-exit surface of the light source 44, a light-entrance surface of the camera unit 42 and optionally an opening of the distal end region 46 of the work channel or rinsing channel. Flexible conductor tracks and/or other electrical or optical lines connect the assembly 40 through the shaft tube 20 to a proximal end of the endoscope 10 not depicted in FIG. 1.

An optical separation layer, indicated by a dark line in FIG. 1, may be provided between the camera unit 42 and the light source 44 and suppress a direct transfer of illumination light from the light source 44 to the camera unit 42.

The assembly 40 is mechanically twice connected to the shaft tube 20. The plastic cladding 50 is integrally bonded to the shaft tube 20 and, by virtue of also filling the lateral opening 26 in the shaft tube 20, also connected in interlocking fashion. Further, the plastic cladding 50 has a mechanical integral bond-type and optionally also interlocking connection with the assembly 40. Consequently, the plastic cladding 50 mechanically and rigidly connects the assembly 40 to the shaft tube 20. Further, the assembly 40 is mechanically connected to the shaft tube 20 by way of the tongue-shaped extension before the plastic cladding 50 is formed.

Figure 2:
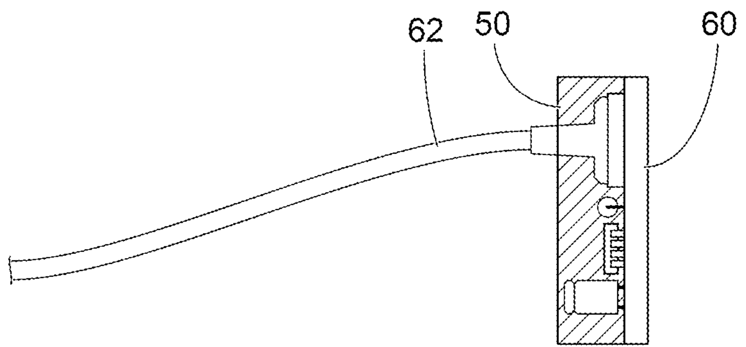
FIG. 2 shows a schematic illustration of an assembly for a proximal end of an endoscope.

FIG. 2 shows a schematic illustration of an exemplar assembly 60 provided for arrangement in a handle at a proximal end of a mediastinoscope or any other endoscope. The assembly 60 has a horseshoe-like or semi-circular arc-shaped form in a plane orthogonal to the plane of the drawing of FIG. 2.

In addition to a printed circuit board with electronic and electro-optic structural elements, the assembly 60 comprises a plastic cladding 50. The plastic cladding 50 covers the printed circuit board and encloses the electronic and electro-optic structural elements. As a result, the plastic cladding 50 protects the printed circuit board and the structural elements from mechanical action, from physical action (for example, contact with a current-carrying object) and from chemical action of a surrounding fluid. Further, the plastic cladding 50 encloses a proximal end of optical fibers 62 and connects these to the printed circuit board in an integrally bonded and/or interlocking fashion. As a result, the plastic cladding 50 creates a permanent mechanical connection between the assembly 60 and the proximal end of the optical fibers 62. In the process, the plastic cladding also prevents, in particular, an ingress of a fluid between the ends of the optical fibers 62 and an electro-optic component of the assembly 60.

In the illustrated example, the plastic cladding 50 covers the assembly 60 only on one side. Deviating from the illustration in FIG. 2, the plastic cladding 50 may also cover the assembly 60 on a plurality of sides, or completely envelope the latter.

The plastic cladding 50 is a plastic component which, in particular, is produced directly on the remaining constituent parts of the assembly 60 by way of a casting process and, in the process, is integrally bonded and/or connected in interlocking fashion therewith from the outset.

Figure 3:
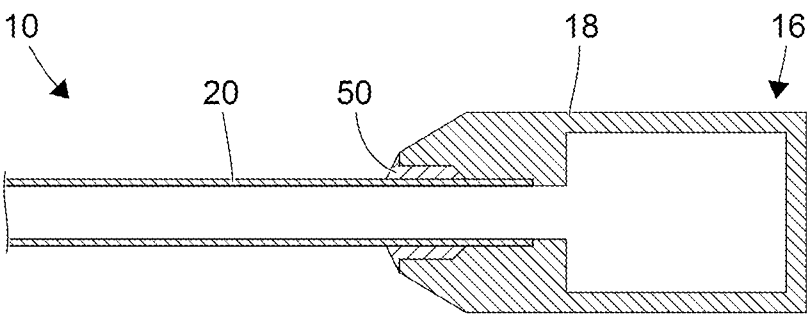
FIG. 3 shows a schematic illustration of a proximal end region of an endoscope.

FIG. 3 shows a schematic illustration of a proximal end region 16 of an endoscope 10. The proximal end region 16 is formed by a handling device 18. A proximal end of the shaft tube 20 is arranged in a corresponding cutout in the distal end of the handling device 18.

A plastic cladding 50 surrounds the transition region between the shaft tube 20 and the handling device 18 and fills the ring-shaped gap between the two. The plastic cladding 50 creates an integral bond-type, mechanical connection between the proximal end of the shaft tube 20 and the distal end of the handling device 18 and prevents an ingress of a fluid between the two.

The plastic cladding 50 is a plastic component which, in particular, is produced directly in the ring-shaped gap between the proximal end of the shaft tube 20 and the distal end of the handling device 18 and which, in the process, is integrally bonded and/or connected in interlocking fashion to the latter.

Figure 4:
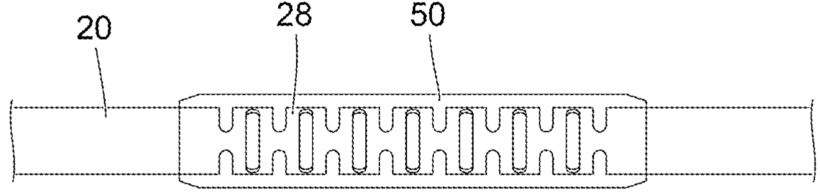
FIG. 4 shows a schematic illustration of a joint region of an endoscope.

FIG. 4 shows a schematic illustration of a flexible joint region of the shaft tube 20 of a medical instrument. In the depicted example, the flexible joint region 28 of the shaft tube 20 is formed by numerous flexible webs between numerous cutouts. As an alternative and deviating from the illustration in FIG. 4, the flexible joint region 28 of the shaft 14 may be formed by one or more pairs of sliding surfaces resting against one another.

The flexible joint region 28 is cladded by a flexible plastic cladding 50. The plastic cladding prevents an ingress of a fluid into the joint region 28.

The plastic cladding 50 is a plastic component which, in particular, is produced directly on the flexible joint region 28 and, in the process, is integrally bonded and/or connected in interlocking fashion therewith from the outset.

Figure 5:
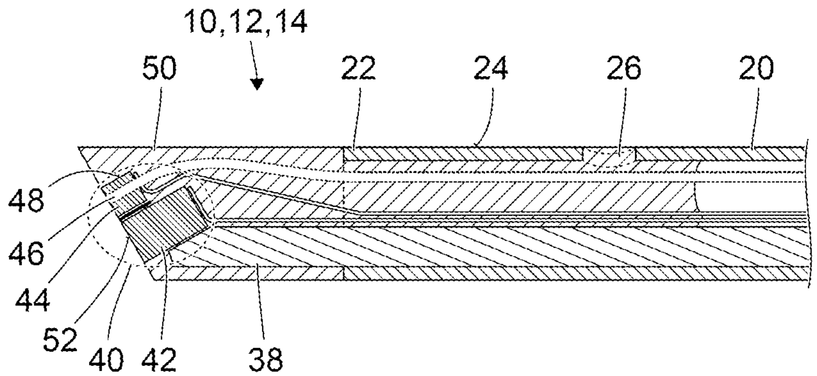
FIG. 5 shows a schematic illustration of a distal end of a further endoscope.

FIG. 5 shows a schematic illustration of a section through a distal end region 12 of an endoscope 10, specifically of the shaft 14 of the endoscope 10. The sectional plane of FIG. 5 corresponds to the sectional plane of FIG. 1. The endoscope

10 shown in FIG. 5 is similar to the endoscope presented on the basis of FIG. 1 in terms of a few features, properties, and functions. Features, properties, and functions in terms of which the endoscope shown in FIG. 5 differs from the endoscope presented in FIG. 1 are described below.

The endoscope 10 shown in FIG. 5 differs from the endoscope presented on the basis of FIG. 1 in that, in particular, no tongue-shaped extension is provided at the distal end 22 of the shaft tube 20. Instead, a heat pipe 38 is arranged in the shaft tube 20. The proximal end of the heat pipe 38, not visible in FIG. 5, is arranged at a proximal end of the endoscope 10, in particular. The distal end of the heat pipe 38 is thermally coupled to the assembly 40. To this end, the distal end of the heat pipe 38 is mechanically connected to the assembly 40 directly or indirectly. In this case, a distal end region of the heat pipe 38 at the same time forms a connecting device for mechanically connecting the assembly 40 to the shaft tube 20, in particular to the distal end 22 of the shaft tube 20.

FIGS. 6 to 13 are used to present a method and a mold for producing one of the plastic claddings 50 from FIGS. 1 to 4. By way of example, the production of the plastic cladding 50 on the distal end 12 of an endoscope 10, depicted on the basis of FIG. 1, is described.

Figure 6:
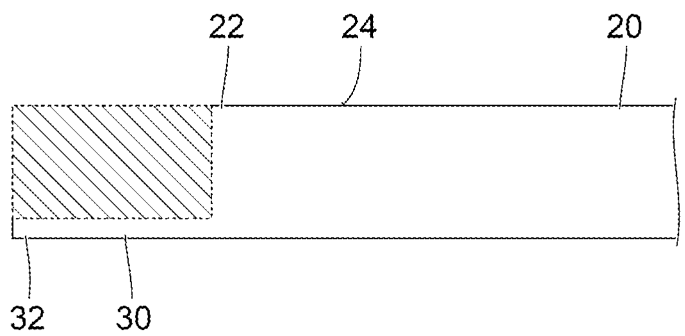
FIG. 6 shows a schematic illustration of a tube as a semifinished product for a shaft tube.

FIG. 6 shows a schematic representation of a tube, from which a shaft tube 20 is manufactured. In particular, the tube exhibits an annular cross section. The longitudinal axis and, in the case of an annular cross section, the axis of symmetry of the tube is parallel to the plane of the drawing of FIG. 6.

The hatching in the figure indicates a region that is removed in order to lay open the distal end 22 of the shaft tube 20 and the tongue-shaped extension 30.

Figure 7:
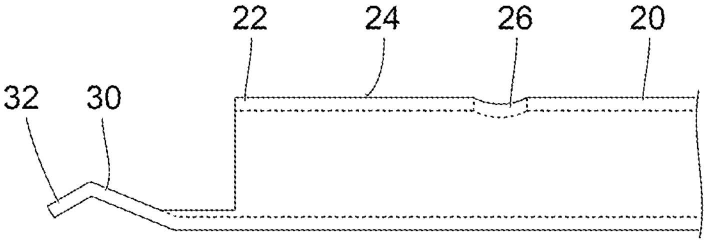
FIG. 7 shows a schematic illustration of a shaft tube with a connecting device.

FIG. 7 shows a schematic illustration of the shaft tube 20 in a later stage of the method. The type of representation, in particular the plane of the drawing, corresponds to that of FIG. 6. Unlike in FIG. 6, the inner contours of the shaft tube 20 are represented by dashed lines.

The region depicted by hatching in FIG. 6 has been removed, and so the distal end 22 of the shaft tube 20 and the tongue-shaped extension 30 have been developed. The tongue-shaped extension 30 is deformed such that it now has two bends. The proximal bend of the tongue-shaped extension creates a distance between the distally adjoining regions of the tongue-shaped extension 30 and the distally continued outer lateral surface of the shaft tube 20 indicated by dashed lines. The distal bend of the tongue-shaped extension 30 causes the distal end 32 of the tongue-shaped extension 30 to have a predetermined orientation relative to the shaft tube 20.

Figure 8:
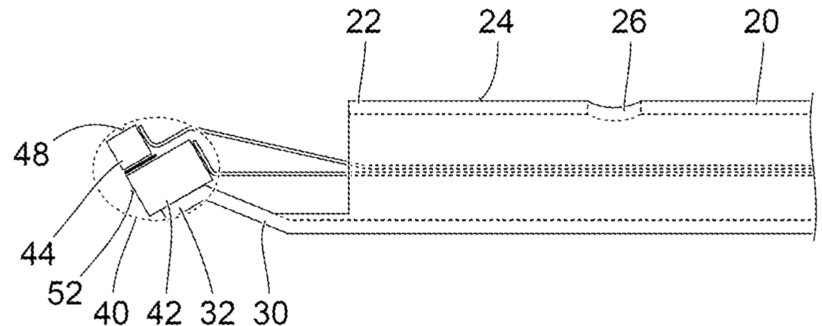
FIG. 8 shows a schematic illustration of the shaft tube from FIG. 7 with an assembly at the connecting device.

FIG. 8 shows a further schematic illustration of the shaft tube 20. The type of representation, in particular the sectional plane, corresponds to that of FIG. 7. Like in FIG. 7, the inner contours of the shaft tube 20 are represented by dashed lines.

The assembly 40 with the camera unit 42 and the light source 44 is permanently mechanically connected to the distal end 32 of the tongue-shaped extension 30, for example by adhesive bonding.

Figure 9:
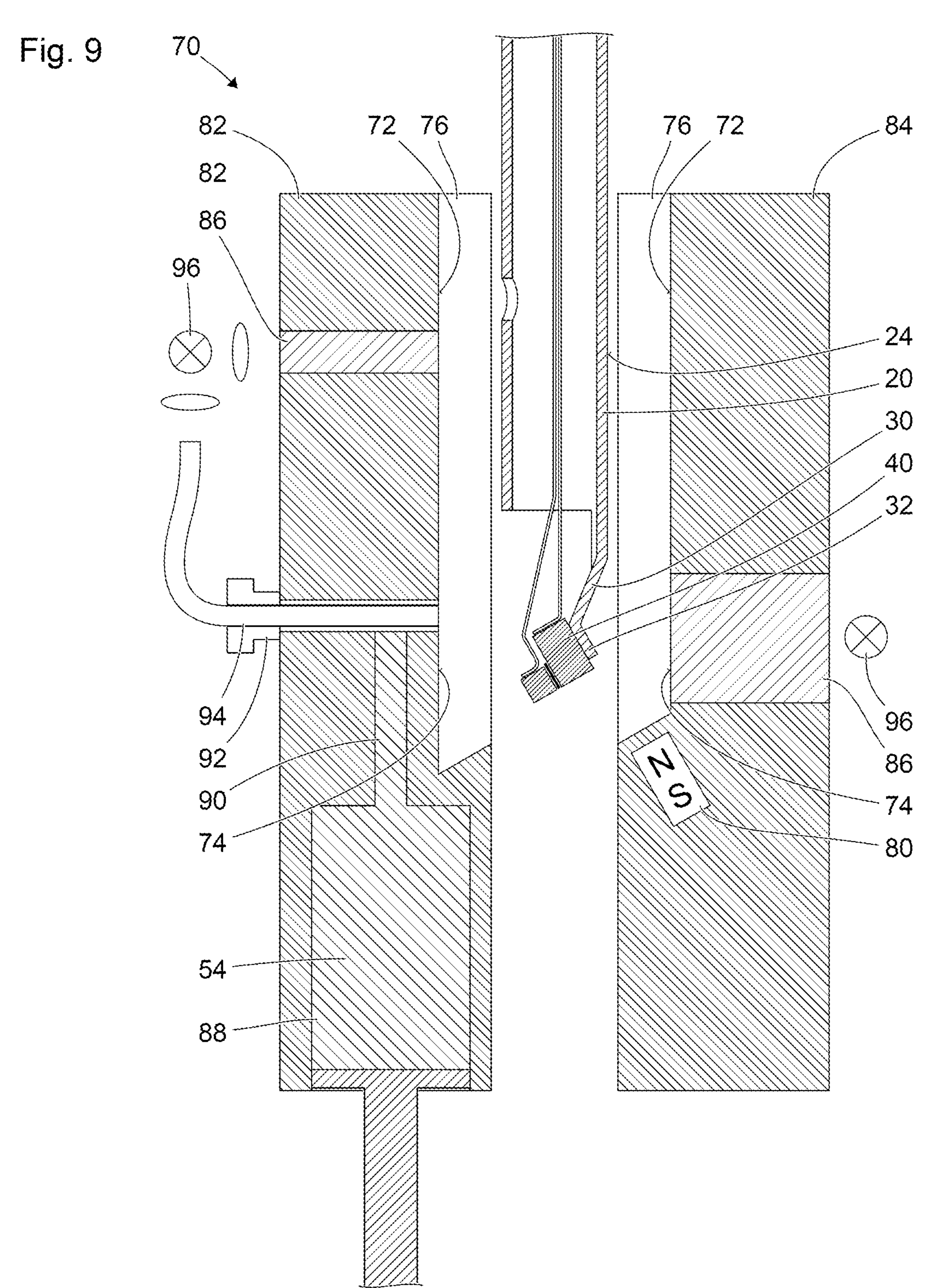
FIG. 9 shows a schematic illustration of the shaft tube and the assembly from FIG. 8 in an open casting mold.

FIG. 9 shows a schematic illustration of the unit of the shaft tube 20 and assembly 40, shown in FIG. 8, at the distal end 32 of the tongue-shaped extension 30 of the shaft tube 20. The unit of shaft tube 20 and assembly 40 is depicted in an open casting mold 70. The shaft tube 20, the assembly 40 and the casting mold 70 are depicted in a section along a plane parallel to the planes of the drawing of FIGS. 1, 6, 7 and 8. The sectional plane of FIG. 9 contains the axis of symmetry of the shaft tube 20.

The casting mold 70 has a mold surface with a first region 72 for planar contact with the outer surface 24 of the shaft tube 20, and a second region 74. The mold surface 72, 74 surrounds a cavity 76, which in the open state of the casting mold 70 depicted in FIG. 9 comprises two portions.

The casting mold 70 comprises a first mold part 82 and a second mold part 84, which each have a share of both the first region 72 of the mold surface and the second region 74 of the mold surface. The mold parts 82, 84 have mold inserts 86, which each form part of the first region 72 or the second region 74 of the mold surface of the casting mold and which reach as far as the outer surface regions of the casting mold 70 in the illustrated example. The mold inserts 86 are manufactured from materials that are transparent to electromagnetic radiation with predetermined spectral properties. Consequently, electromagnetic radiation can be coupled into the cavity 76 through the mold insert 86.

The casting mold 70 has a supply device 88 for supplying liquid plastic 54 to the cavity 76. The supply device 88 may consist of a fluid connector that may be able to be connected or may be connected to a heating and metering device for liquefying a thermoplastic and for metering the liquefied plastic. Alternatively, the supply device may comprise a heating and metering device for liquefying and metering a thermoplastic, said supply device being able to be integrated in the casting mold 70.

By contrast, the casting mold 70 depicted in FIG. 9 is provided for a plastic that is not a thermoplastic, but rather one that is liquid at room temperature, and the solidification of which is caused or triggered by the action of electromagnetic radiation in a predetermined wavelength range. Therefore, the supply device 88 does not comprise a heating device but only a metering device for the liquid plastic. The metering device is indicated by a piston in a cylindrical cavity.

A supply channel 90 connects the supply device 88 to the cavity 76 of the casting mold 70. The supply channel 90 is T-shaped in the illustrated example. A sliding plug element, referred to throughout as a "slider", 92 with an optically transparent core 94 within a sleeve made of a mechanically robust material, for example steel, is arranged in the supply channel 90 and is able to slide longitudinally along one arm of the supply channel 90. The slider 92 is guided in the supply channel 90 with little play and friction and can adopt various positions. In FIG. 9, the slider 92 is depicted in a position in which the end thereof facing the cavity 76 forms part of the mold surface of the casting mold 70, specifically part of the second region 74 of the mold surface. At the end distant from the cavity 76, the optically transparent core 94 merges into the light guiding cable which is optically coupled to a light source 96.

Further, a magnet 80 is arranged in the second mold part 84 of the casting mold 70. In the illustrated example, the magnet 80 is a permanent magnet which is embedded in the mold part 84. Alternatively, the magnet 80 may be arranged at, and in particular fastened to, an outer surface of the casting mold 70, and/or be in the form of an electromagnet.

Figure 10:
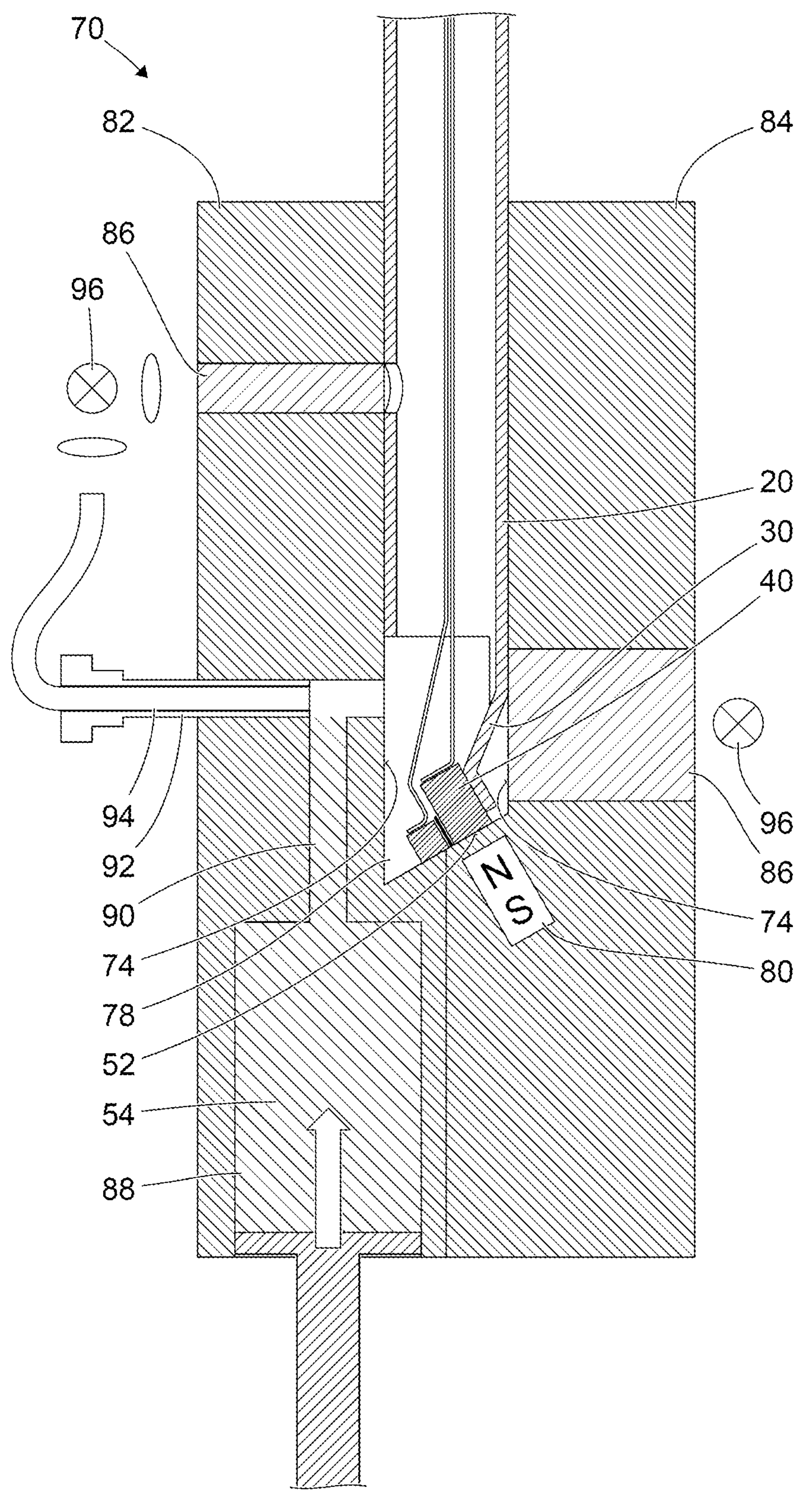
FIG. 10 shows a further schematic illustration of the casting mold from FIG. 9.

FIG. 10 shows a further schematic illustration of the unit of shaft tube 20 and assembly 40, and the casting mold 70. The type of representation corresponds to that of FIG. 9.

FIG. 10 depicts the casting mold 70 closed and the unit of shaft tube 20 and assembly 40 is arranged in the cavity of the casting mold 70 in a predetermined position and with a predetermined orientation. In this case, the outer surface 24 (cf. FIG. 9) of the shaft tube 20 extensively contacts the first region 72 of the mold surface of the casting mold 70. The second region 74 of the mold surface of the casting mold 70 bounds a casting chamber 78, which merges into the lumen of the shaft tube 20.

Arranged in the casting chamber 78 is the assembly 40, the distal end surface 52 of which extensively contacts the second region 74 of the mold surface of the casting mold 70. To ensure the planar contact of the distal end surface 52 of the assembly 40 on the second region 74 of the mold surface of the casting mold 70, the shaft tube 20 is arranged in the casting mold 70 and the tongue-shaped extension at the distal end 22 of the shaft tube 20 is dimensioned in such a way that the tongue-shaped extension is elastically deformed and its elastic restoring force presses the distal end surface 52 of the assembly 40 against the second region 74 of the mold surface of the casting mold 70. Alternatively or in addition, the magnet 80 produces an attractive force at the distal end 32 of the tongue-shaped extension 30 at the distal end 22 of the shaft tube 20 and/or at the assembly 40 such that the distal end face 52 thereof is pressed extensively against the second region 74 of the mold surface of the casting mold 70.

In the predetermined position of the unit made of shaft tube 20 and assembly 40 in the casting mold 70 shown in FIG. 10, the lateral opening 26 in the shaft tube 20 is flush with one of the transparent mold inserts 86. Electromagnetic radiation produced by a light source 96 can therefore be coupled into the lumen of the shaft tube 20 through this transparent mold insert 86 and through the lateral opening 26. The second transparent mold insert 86 is arranged in the region of the casting chamber 78 such that electromagnetic radiation from a light source 96 can be coupled into the casting chamber 78 through this second transparent mold insert 86.

In FIG. 10, the slider 92 is depicted in the supply channel 90 in a position distant from the casting chamber 78, the supply channel 90 forming an open connection between the supply device 88 and the casting chamber 78 in said position. As a result of the movement of the piston of the supply device 88, as indicated by an arrow, liquid plastic can be displaced from the supply device 88 and forced into the casting chamber 78 through the supply channel 90.

Figure 11:
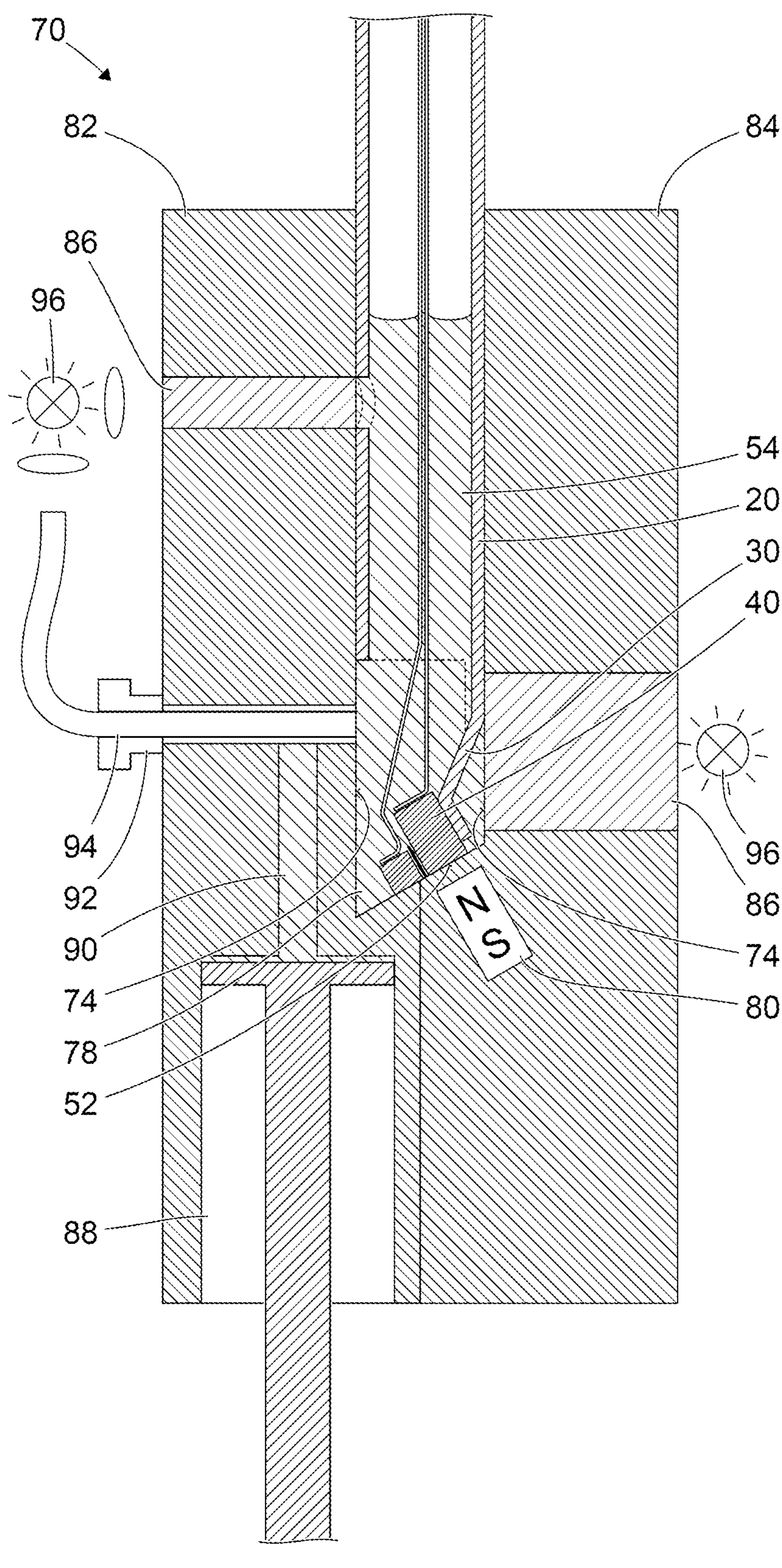
FIG. 11 shows a further schematic illustration of the casting mold from FIGS. 9 and 10.

FIG. 11 shows a further schematic illustration of the unit of shaft tube 20 and assembly 40 in the casting mold 70. The type of representation corresponds to that of FIGS. 9 and 10.

FIG. 11 shows a situation in which, by means of the supply device 88, the casting chamber 78 has been completely filled with liquid plastic and the lumen of the shaft tube 20 has been filled with liquid plastic to such an extent that the lateral opening 26 in the shaft tube 20 is also filled with the liquid plastic 54. The slider 92 has once again been inserted fully into the supply channel 90 such that the end of the slider facing the casting chamber 78 forms part of the second region 74 of the mold surface of the casting mold 70.

In this situation, the light sources 96 are activated for the purposes of producing light, that is, electromagnetic radiation with a predetermined wavelength, said light being coupled into the liquid plastic 54 through the transparent mold inserts 86 and through the transparent core 94 of the slider 92. The light causes the solidification of the liquid plastic 54, for example by way of polymerization. Alternatively, the light triggers solidification of the liquid plastic 54, for example by releasing a catalyst that brings about or accelerates polymerization.

Figure 12:
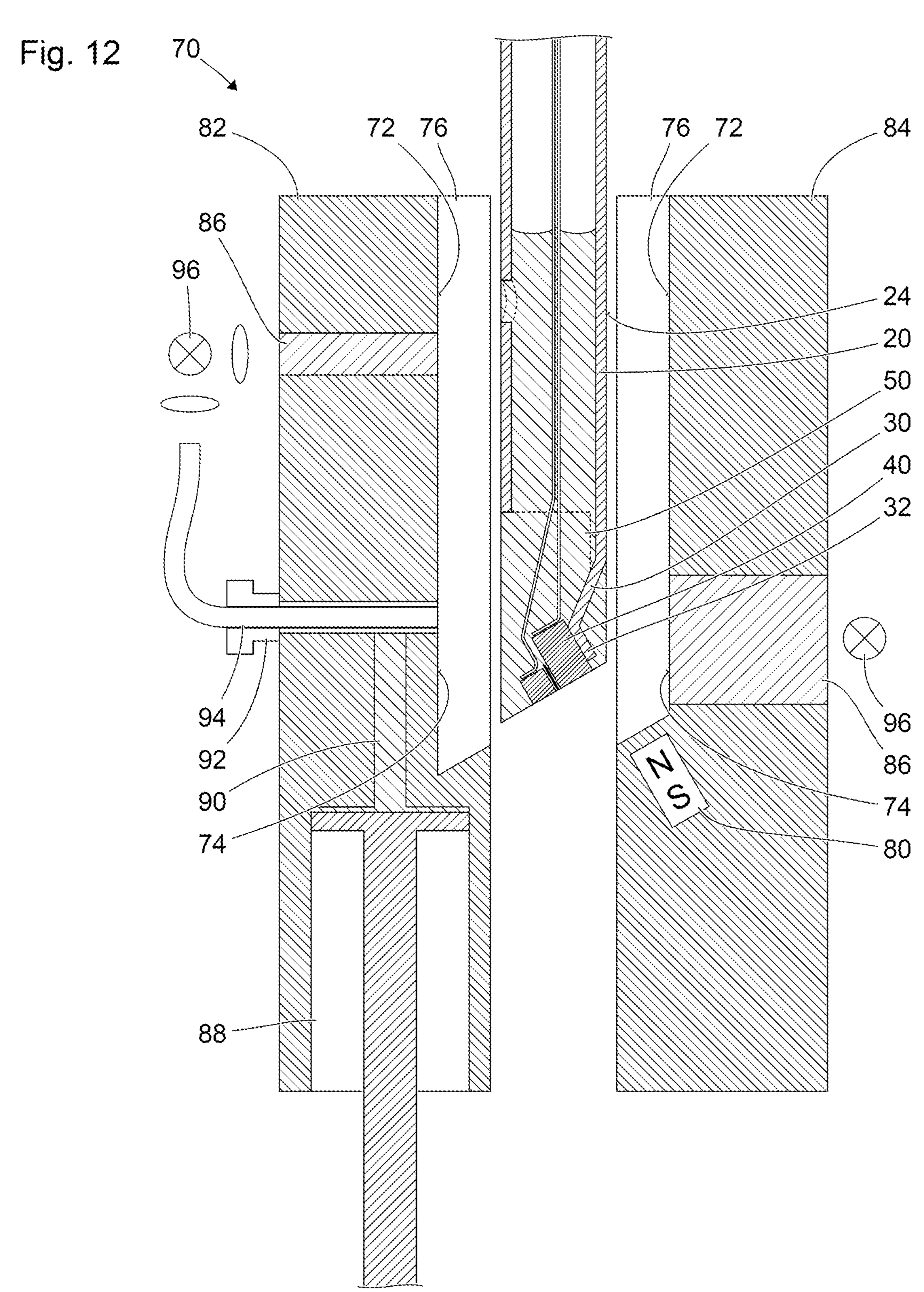
FIG. 12 shows a further schematic illustration of the casting mold from FIGS. 9 to 11.

FIG. 12 shows a further schematic illustration of the unit of shaft tube 20 and assembly 40, and the casting mold 70. The type of representation in FIG. 12 corresponds to that of FIGS. 9 to 11.

The liquid plastic has solidified to form the solid plastic cladding 50 by the aforementioned action of electromagnetic radiation, the plastic cladding enclosing the assembly 40 and the tongue-shaped extension 30, protruding into the shaft tube 20, being integrally bonded to the shaft tube 20, and further being connected to said shaft tube in interlocking fashion by way of engagement in the lateral opening 26 in the shaft tube 20. The casting mold 70 is open, and the shaft tube 20 with the completed distal end can be removed.

For the production of a plastic component or plastic cladding 50 as depicted on the basis of FIGS. 2 to 4, the casting mold has features and properties that deviate from those presented on the basis of FIGS. 9 to 12. This includes an appropriate geometric design of the region 74 of the mold surface bounding the casting chamber 78, specifically a geometric design corresponding to the outer surface of the plastic component or of the plastic cladding 50 to be produced. This further includes an appropriate geometric design of the region 72 of the mold surface bounding the casting chamber 78, specifically a geometric design corresponding to the lateral surface 24 of the shaft 20 (cf. FIGS. 2, 3), the handling device 18 (cf. FIG. 3), the assembly 60 and the proximal end of the optical fibers 62 (cf. FIG. 4). To this end and as illustrated on the basis of FIGS. 9 to 12, the cavity 76 of the casting mold may have an opening at one end, through which the shaft tube 20 extends out of the casting mold, or may be open at two ends, such that, for example in the case of the exemplary embodiment of FIG. 4, said shaft tube can protrude from both ends.

FIG. 13 shows a schematic flow chart of a method for supplementing a component of a medical instrument with a plastic component, in particular a plastic cladding. The method can be carried out using a casting mold 70 having the features, properties and functions presented on the basis of FIGS. 9 to 12 or using a casting mold with features, properties and functions deviating therefrom. The method can be used to produce a medical instrument with features, properties and functions presented on the basis of FIG. 1, 2, 3, 4, 5 or a medical instrument with features, properties and functions deviating therefrom. Reference signs from FIGS. 1 to 12 are used below in exemplary fashion. The method is presented in exemplary fashion on the basis of a shaft tube that should be supplemented with a plastic component.

A tube provided for the formation of a shaft tube 20 is provided in a first step 101. A part is removed from one end of the tube in an optional second step 102 in order to lay open and form a distal end 22 of the shaft tube 20 and a tongue-shaped extension 30, respectively. The tongue-shaped extension 30 is deformed, more particularly bent, in an optional third step 103.

Alternatively, a shaft tube 20 is provided with a joint region. By way of example, this is implemented by forming cutouts, between which narrow elastic webs remain. Alternatively, a joint region may comprise one or more interlocking joints, which each facilitate pivoting or tilting about one or two axes.

In a fourth step 104, an assembly 40 or a handling device 18 or any other assembly that is to be connected to the shaft tube 20 by way of a plastic cladding is provided. In a fifth step 105, the assembly 40 or the handling device 18 is mechanically connected to the shaft tube 20. By way of example, this is implemented by way of adhesive bonding, or else merely by a plug-in connection, which only brings about an alignment between firstly the shaft tube 20 and secondly the assembly 40 or the handling device 18.

If the method is intended to clad a joint region of the shaft, the fourth step 104 and the fifth step 105 may also be dispensed with.

In the case of a sixth step 106, the shaft tube 20 is inserted into a casting mold 70 together with the assembly 40 or the handling device 18. The casting mold 70 is closed in a seventh step 107. Subsequently, the shaft tube 20 may protrude from the casting mold 70 on one side or on two opposing sides. In the case of the connection to a handling device, the handling device may also protrude from the casting mold 70.

In an eighth step 108, liquid plastic is supplied to a casting chamber 78 through a supply channel 90. In a ninth step 109, a slider 92 in the supply channel 90 is moved in order to close the supply channel.

A force is exerted on the assembly 40 in an optional tenth step 110 in order to move said assembly into a predetermined position, for example with extensive contact to a region 74 of the mold surface of the casting mold 70. By way of example, the force may be an elastic restoring force of a tongue-shaped extension, as a mechanical connecting device, on account of an elastic deformation during the inserting 106 and/or closing 107 step. Alternatively, the force can be generated by a magnet, for example.

Deviating from the presentation of FIG. 13, the exertion of force may already have started before the supply of the liquid plastic in order to prevent an ingress of the liquid plastic into a gap between assembly and mold surface.

During an eleventh step 111, which is carried out during the tenth step 110, electromagnetic radiation is coupled into the liquid plastic 54 in order to bring about or trigger a solidification of the liquid plastic 54 to form a solid plastic cladding 50.

The force exerted in the tenth step is usually exerted at least until the complete solidification of the initially liquid plastic.

The casting mold 70 is opened in a twelfth step 112. The shaft tube 20 with the plastic cladding 50 is removed in a thirteenth step 113.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein. Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

REFERENCE SIGNS

10 Medical instrument
12 Distal end region of the medical instrument 10
14 Shaft of the medical instrument 10
16 Proximal end region of the medical instrument 10
18 Handling device at the proximal end region 16 of the medical instrument 10
20 Shaft tube
22 Distal end of the shaft tube 20
24 Lateral surface of the shaft tube 20
26 Lateral opening in the shaft tube 20
28 Flexible joint region of the shaft 14
30 Tongue-shaped extension at the distal end 22 of the shaft tube 20
32 Distal end of the tongue-shaped extension 30
38 Heat pipe
40 Assembly at the distal end 12 of the medical instrument 10
42 Camera unit
44 Light source, more particularly light-emitting diode, for producing illumination light
46 Distal end region of work channel or rinsing channel
48 Lateral surface region of the assembly 40
50 Plastic cladding of the assembly 40 or 60, or of the flexible joint region 28
52 Distal end surface of the assembly 40
54 Liquid plastic
60 Assembly at the proximal end 16 of the medical instrument 10
62 Optical fibers, optically mechanically connected to the assembly 60
70 Casting mold
72 First region of the mold surface of the casting mold 70
74 Second region of the mold surface of the casting mold 70
76 Cavity of the casting mold 70, bounded by the first region 72 and the second region 74 of the mold surface
78 Casting chamber, bounded by the second region 74 of the mold surface and the component 20
80 Magnet
82 First mold part of the casting mold 70
84 Second mold part of the casting mold 70
86 Transparent mold insert of the second mold part 84
88 Supply device for liquid plastic
90 Supply channel for supplying liquid plastic to the casting chamber 78
92 Slider in the supply channel 90
94 Optically transparent core of the slider 92
96 Light source
101 First step (providing a shaft tube)
102 Second step (laying open a tongue-shaped extension and a distal end of the shaft tube)
103 Third step (plastically deforming the tongue-shaped extension)
104 Fourth step (providing an assembly)
105 Fifth step (mechanically connecting the assembly to the tongue-shaped extension)
106 Sixth step (inserting the component with the assembly into a casting mold)
107 Seventh step (closing the casting mold)
108 Eighth step (supplying liquid plastic)
109 Ninth step (moving a slider which closes a supply channel for supplying liquid plastic)
110 Tenth step (exerting a force on the assembly)
111 Eleventh step (coupling electromagnetic radiation into the liquid plastic in order to trigger solidification)
112 Twelfth step (opening the casting mold)
113 Thirteenth step (removing the shaft tube with plastic cladding made of solidified plastic)

The invention claimed is:

1. A method for supplementing a component of a medical instrument with a plastic component, comprising:

inserting the component and an assembly of the medical instrument into a casting mold and closing the casting mold, a first region of a mold surface of the casting mold being placed against the component, a casting chamber remaining between a second region of the mold surface of the casting mold and the component, and holding the assembly, which is located at a distal end of the medical instrument, against the casting mold with a magnet, with the assembly, which is held by the magnet, also being supported by a tongue shaped extension;

supplying a liquid plastic to the casting chamber; and coupling an electromagnetic radiation into the liquid plastic within the casting chamber to trigger a solidification of the liquid plastic and form the plastic component.

2. The method of claim 1, wherein the electromagnetic radiation is coupled into the liquid plastic through a mold insert in a mold part, where the mold insert is transparent to the electromagnetic radiation, or through a transparent mold part, or through a transparent slider, or through a transparent insert in a slider for closing a supply opening.

3. The method of claim 1, wherein the liquid plastic is supplied to the casting chamber through the component from an end of the component that faces away from the casting chamber.

4. The method of claim 2, wherein the electromagnetic radiation is coupled from an end of the component facing away from the casting chamber into the casting chamber through the component.

5. The method according to claim 1, wherein the insertion of the component comprises an insertion of the assembly, mechanically connected to the component, into the casting mold.

6. The method of claim 5, wherein the insertion of the component into the casting mold comprises an insertion of the assembly, mechanically connected to the component, the assembly having at least an image sensor or any other sensor for acquiring one or more measured values, or a light-emitting diode for generating illumination light or any other light source, or a distal end region of a work channel or rinsing channel or of an optical waveguide, or a handling device.

7. The method according to claim 1, wherein the insertion of the component into the casting mold comprises an insertion of an electronic assembly for arrangement on a proximal end of an endoscope.

8. The method according to claim 1, wherein the insertion of the component into the casting mold comprises an insertion of a joint region.

9. A method comprising:

inserting at least one component of an endoscope and an assembly into a casting mold;

closing the casting mold, a first region of a mold surface of the casting mold being placed against the component, a casting chamber remaining between a second region of the mold surface of the casting mold and the component, and a metal distal end of the assembly being held against a portion of the casting mold by a magnet, with the assembly that is held by the magnet also being supported by a tongue shaped extension;

supplying a liquid plastic to the casting chamber; and applying an electromagnetic radiation to the liquid plastic within the casting chamber to trigger a solidification of the liquid plastic to form a plastic component for the endoscope.

* * * * *